United States Patent [19]

Schroeder et al.

[11] Patent Number: 4,786,727

[45] Date of Patent: Nov. 22, 1988

[54] PREPARATION OF HEXAMETHYLENEIMINE

[75] Inventors: Wolfgang Schroeder, Bad Duerkheim; Wolfgang Franzischka, Ludwigshafen; Herbert Mueller, Frankenthal, all of Fed. Rep. of Germany

[73] Assignee: BASF Aktiengesellschaft, Ludwigshafen, Fed. Rep. of Germany

[21] Appl. No.: 608,447

[22] Filed: May 9, 1984

Related U.S. Application Data

[63] Continuation-in-part of Ser. No. 370,381, Apr. 21, 1982, abandoned, which is a continuation of Ser. No. 59,180, Jul. 20, 1979, abandoned.

[30] Foreign Application Priority Data

Aug. 26, 1978 [DE] Fed. Rep. of Germany ....... 2837290

[51] Int. Cl.$^4$ .......................................... C07D 295/02
[52] U.S. Cl. .................................................. 540/484
[58] Field of Search .................... 260/239 B; 540/484

[56] References Cited

U.S. PATENT DOCUMENTS

| 4,009,124 | 2/1977 | Laurer et al. ...................... 252/463 |
| 4,014,867 | 3/1977 | Yeh et al. ......................... 260/239 B |
| 4,035,353 | 7/1977 | Kanetake et al. ............... 260/239 B |

FOREIGN PATENT DOCUMENTS

| 2347905 | 4/1974 | Fed. Rep. of Germany ... 260/239 B |
| 2459547 | 6/1975 | Fed. Rep. of Germany . |
| 49-86385 | 8/1974 | Japan . |
| 52-128388 | 10/1977 | Japan . |

OTHER PUBLICATIONS

Kanetaka et al., "Chemical Abstracts", vol. 82, 1975, col. 139415a.

Houben-Weyl, "Methoden der Organischen Chemie", vol. 11/1, 1957, 4th Ed., pp. 584–585; 591–592.

Taira, "Chemical Abstracts", vol. 71, 1969, col. 112398h.

Primary Examiner—Glennon H. Hollrah
Assistant Examiner—James H. Turnipseed
Attorney, Agent, or Firm—Keil & Weinkauf

[57] ABSTRACT

Hexamethylenemine is obtained by hydrogenating ε-caprolactam, the latter being vaporized and hydrogenated under a working pressure of less than 10 bar, the gas phase being unsaturated in respect of caprolactam, and the residence time being short.

1 Claim, No Drawings

PREPARATION OF HEXAMETHYLENEIMINE

This application is a continuation-in-part of application Ser. No. 370,381, which was filed on Apr. 21, 1982, now abandoned, which application was a continuation of application Ser. No. 59,180, which was filed on July 20, 1979, which application has been abandoned.

The present invention relates to a process for the preparation of hexamethyleneimine by hydrogenating ε-caprolactam in the gas phase under a pressure on the order of magnitude of atmospheric pressure, e.g. from 1 to 10 bar, and at 170° to 250° C. (preferably about 200° C.). The catalyst contains copper and aluminum oxide and is used as a fixed bed or fluidized bed.

Hexamethyleneimine is an intermediate, for example, for the preparation of crop protection agents. It has been proposed to prepare hexamethyleneimine by the hydrogenation of caprolactam (compare Houben-Weyl, Methoden der organischen Chemie, 4th Edition, Volume 11/1, pages 584–585 and 591–592), but up to now no process which might have found industrial application has been developed. In the processes which have been disclosed, caprolactam is dissolved in a high-boiling solvent and is reacted with hydrogen over a catalyst which is usually in the suspended form. The catalysts disclosed differ in type. According to Japanese Laid-Open Application 49/086,358 (see also J. Ind. Eng. Chem. Prod. Res. Dev. 15/4 (1976), 295 et seq.) relatively expensive cobalt-rhenium-molybdenum catalysts can be used. German Laid-open Application DOS No. 2,459,547 proposes a similar catalyst and states that, advantageously, the hexamethyleneimine formed should be evaporated directly from the reaction mixture in order to prevent its further reaction. According to U.S. Pat. No. 4,014,867 a copper chromite catalyst can be used. Japanese Laid-Open Application No. 77/128,388 proposes Raney cobalt and states the yield to be 88% in isopropanol solution.

The conditions used are, in general, a temperature greater than 200° C. and a pressure greater than 80 bar. It is true that a good yield is alleged to be achieved at low temperatures, but in every case it is necessary not only to purify the reaction product but also to separate off the solvent and work it up to permit its re-use.

It is an object of the present invention to provide a simple process for the preparation of hexamethyleneimine which can be operated substantially without formation of by-products. We have found that this object is achieved by using a particularly active catalyst, which even at a hydrogen pressure corresponding to atmospheric pressure and a relatively low temperature gives yields of 98% or more and—depending on the residence time—a high conversion of the caprolactam. For example, residence times of from 1 to about 100 seconds, especially from 5 to 50 seconds, may be used. Even at a residence time of 10 seconds (calculated from the effective gas volume and based on the empty reactor) a conversion of, for example, 50% is achieved. With increasing hydrogenation temperature, the rate of reaction continues to increase rapidly but at the same time the yield decreases. The most suitable hydrogenation temperature at which high conversion and a good yield are achieved with a reasonable residence time depends, inter alia, on the activity of the catalyst used.

The copper-aluminum oxide catalysts, described in U.S. Pat. No. 4,009,124 are very suitable for the process. The catalyst described in the patent is formed by precipitating at a pH of 8 to 9.5 and at a temperature of from 60° to 90° C., a. an aqueous dilute solution of copper and aluminum salts capable of being precipitated by carbonate, the copper and aluminum being present in said solution in an atomic ratio of m:6, m being a number between 2 and 6, with
b. an aqueous alkali metal carbonate or bicarbonate solution, the atomic concentration of alkali being about twice the concentration of copper and aluminum in said solution, whereby a composition is obtained of the formula $$Cu_mAl_6(CO_3)_{0.5m}O_3(OH)_{m+12}$$

where m is an integer between 2 and 6. The precipitate is thereafter dried and annealed at 350° to 600° C. Reference may be made to the said patent for further details in this context. A temperature of from 170° to 250° C. (on the order of 200° C.), a residence time of less than 1 minute and a working pressure of 10 bar or less are regarded to be the most suitable conditions for these catalysts. However, with this residence time it must be borne in mind that a gas phase reaction requires a relatively high reaction volume, if a short residence time is not achievable.

Increasing the partial pressure of hydrogen while keeping the total pressure constant has the effect that for a given conversion the residence time is reduced and hence the throughput per unit amount of catalyst is increased, or that for a given residence time the conversion and hence again the throughput per unit amount of catalyst is increased. This due to the fact that the achievable throughput per unit amount of catalyst (in the present case generally at least 0.1 kg of caprolactam per liter of catalyst per hour) depends, at a given gas pressure, on the vapor pressure of the caprolactam and the volumetric flow rate of the hydrogen used for the hydrogenation.

Since the temperature determines the vapor pressure of the caprolactam, the throughput per unit amount of catalyst can only be varied by varying the amount of hydrogen, the hydrogen usually being recycled; such variation alters the residence time for a given catalyst volume. Accordingly, the residence time is a critical parameter in the process according to the invention. On the other hand, the above considerations also show that the process has the advantage that it is particularly simple and easy to regulate.

The process according to the invention is therefore advantageously carried out as follows:

Sufficient caprolactam is added to a circulating stream of hydrogen (for example by injection or spraying into the latter), the hydrogen being preheated if appropriate, to ensure that, after evaporation of the caprolactam, the calculated vapor pressure amounts to about 50–70% of the saturation vapor pressure at the hydrogenation temperature. Before entering the catalyst bed, the mixture thus obtained is brought to the hydrogenation temperature (advantageously by passing in counter-current to the gases which leave the reactor by or conducting the mixture in a cooling tube through the catalyst bed and in doing so the caprolactam is completely vaporized). The proportion by volume of caprolactam in the gas phase is at that stage about 10%. This gas mixture is allowed to flow, for example vertically, through the catalyst bed at a flow rate of from 5 to 50 cm/sec. Because of the relatively low concentration of caprolactam, the temperature rise is only a few degrees. The gas stream which issues is cooled in order to separate out the hexamethyleneimine and unconverted caprolactam. This cooling can also be carried out in several stages. For example, the mixture is first cooled to about 50° C., so that residual caprolactam, together with minor amounts of hexamethyleneimine, separates out as a liquid. In the second stage, the mixture is cooled, if appropriate stepwise to −25° C. Hereupon, virtually the entire hexamethyleneimine, water and residual traces of caprolactam separate out.

The two condensates can be worked up conjointly or separately, and in doing so the unconverted caprolactam can be recovered and recycled. Advantageously, the condensate from the first cooling stage is recycled directly to the reaction.

EXAMPLE 1

To carry out the process, an iron tube of about 4 liters capacity, equipped with a heated jacket, is provided with a thin-walled pipe coil, terminating in the vicinity of the bottom of the reaction tube and connected, via a heater, to a melting vessel and a hydrogen feed. A condenser and separator are provided for the gas leaving the reactor. The separator is followed by a water cooler and a brine cooler which in turn is followed by a separator for the greater part of the useful product. The residual gases from are used to pre-cool the feed gases and are then recycled.

The catalyst introduced into the reactor consists of a copper/aluminum oxide catalyst as described in U.S. Pat. No. 4,009,124, in the form of cylindrical tablets 3 mm thick and with a diameter of 3 mm. The catalyst is pre-reduced with nitrogen containing 3% of hydrogen, starting at 120° C. and gradually raising the temperature to 200° C. When no further water is formed, the catalyst is after-treated with pure hydrogen for several hours. To obtain the required reaction temperature, the jacket is fed with a high-boiling organic heat transfer medium.

The hydrogen flow is set to 2,000 liters/hour, resulting in a pressure of about 1.05 bar at a temperature of 190° C.

Immediately before the hydrogen enters the reactor, 400 ml per hour of a caprolactam melt, preheated to 130°–150° C., are fed into the stream of hydrogen. The mixture flows downwardly in the feed line and by the time it reaches the exit the caprolactam has vaporized completely. The mixture then flows through the catalyst bed, where a part of the caprolactam is hydrogenated. From the stated volumes and temperatures, the residence time in the bed is calculated to be about 5 seconds. The gas mixture leaving the reactor is cooled in two states: at about 50°–70° C., a mixture consisting principally of caprolactam separates out (condensate 1). In the second stage, the gas reaches a temperature of from about 0° to −10° C., and a mixture (which remains liquid at the said temperature) of hexamethyleneimine and the water formed separates out (condensate 2).

The amount of substance which condenses in the first cooling stage corresponds to two-thirds of the weight of caprolactam; the condensate consists of 95.3% of caprolactam, 4.1% of hexamethyleneimine and 0.6% of by-products. The remaining one-third by weight (condensate 2) consists of 80.2% of hexamethyleneimine, 16.4% of water, 3.3% of caprolactam and 0.1% of other compounds.

Accordingly, the conversion of caprolactam is 33% and the selectivity achieved is about 99%.

EXAMPLE 2

The procedure followed is as described in Example 1 except that the temperature in the reactor is set to 200° C. The amount of condensate 1 corresponds to one-third of the caprolactam employed, and the condensate consists of 93.2% of caprolactam, 3% of hexamethyleneimine and 3.8% of other compounds. The condensate 2 consists (ignoring the water present) of 96.9% of hexamethyleneimine, 2.2% of caprolactam and 1% of other compounds. From these weight data, the conversion is calculated to be 67% and the selectivity 97–98%.

We claim:

1. A process for the preparation of hexamethyleneimine by hydrogenating ε-caprolactam over a copper-/aluminum oxide hydrogenation catalyst which is fixed or forms a fluidized bed, said catalyst being formed by precipitating, at pH 8 to 9.5 and a temperature of from 60° to 90° C.
   a. an aqueous dilute solution of copper and aluminum salts capable of being precipitated by carbonate, the copper and aluminum being present in said solution in an atomic ratio of m:6, m being a number between 2 and 6, with
   b. an aqueous alkali metal carbonate or bicarbonate solution, the atomic concentration of alkali being about twice the concentration of copper and aluminum in said solution, whereby a composition is obtained of the formula $$Cu_mAl_6(CO_3)_{0.5m}O_3(OH)_{m+12},$$

having the above definition, and thereafter drying and annealing the precipitate at 350° to 600° C., wherein the reaction is carried out in the gas phase and the caprolactam is vaporized in the stream of hydrogen gas, in an amount such that at a hydrogenation reaction temperature of from 170° to 250° C. and under a working pressure of 10 bar or less the degree of saturation with caprolactam is less than 80%, the residence time being less than one minute.

* * * * *